(12) United States Patent
Jeannin et al.

(10) Patent No.: US 7,226,455 B2
(45) Date of Patent: Jun. 5, 2007

(54) INJECTOR FOR A FLEXIBLE IMPLANT

(75) Inventors: Lionel Jeannin, Annecy le Vieux (FR); Gilles Bos, La Balme de Sillingy (FR)

(73) Assignee: Corneal Industrie, Pringy (FR)

( * ) Notice: Subject to any disclaimer, the term of this patent is extended or adjusted under 35 U.S.C. 154(b) by 683 days.

(21) Appl. No.: 10/606,634

(22) Filed: Jun. 26, 2003

(65) Prior Publication Data
US 2005/0251236 A1   Nov. 10, 2005

Related U.S. Application Data

(63) Continuation of application No. 10/295,622, filed on Nov. 15, 2002, now abandoned.

(30) Foreign Application Priority Data

May 19, 2000 (FR) .................................. 00 06417
May 17, 2001 (WO) ...................... PCT/FR01/01510

(51) Int. Cl.
*A61F 9/00* (2006.01)
*A61F 2/16* (2006.01)
(52) U.S. Cl. ..................... 606/107; 606/107; 128/899; 623/6.11
(58) Field of Classification Search ................ 606/107; 128/898; 623/6.11
See application file for complete search history.

(56) References Cited

U.S. PATENT DOCUMENTS

| | | |
|---|---|---|
| 4,165,746 A | 8/1979 | Burgin |
| 4,976,716 A | 12/1990 | Cumming |
| 5,052,402 A | 10/1991 | Bencini et al. |
| 5,454,818 A | 10/1995 | Hambleton et al. |
| 5,630,841 A * | 5/1997 | McDonald .................. 128/898 |
| 5,653,753 A * | 8/1997 | Brady et al. ................ 606/107 |

FOREIGN PATENT DOCUMENTS

| | | |
|---|---|---|
| EP | 0 363 213 A2 | 10/1989 |
| EP | 0 340 698 A2 | 11/1989 |

* cited by examiner

*Primary Examiner*—Vy Bui
(74) *Attorney, Agent, or Firm*—Cohen Pontani Lieberman & Pavane LLP

(57) ABSTRACT

The invention relates to a folder module for folding a flexible intraocular implant for injection into the eye of a patient. The module comprises two jaws that are movable relative to each other, each jaw having a folder wall constituted by a portion of a cylindrical surface, and a plane wall secured to the folder wall, the two plane walls lying in parallel planes;

a pivot axis orthogonal to the plane walls to control relative pivoting movement of one jaw relative to the other;
  one of the jaws being capable of occupying relative to the other a first position in which said plane walls are offset relative to each other;
  a second position in which the plane walls face each other so as to define an implant confinement volume; and
  a third position in which the folder walls meet each other to define a folder chamber enabling the implant to be finally folded.

10 Claims, 3 Drawing Sheets

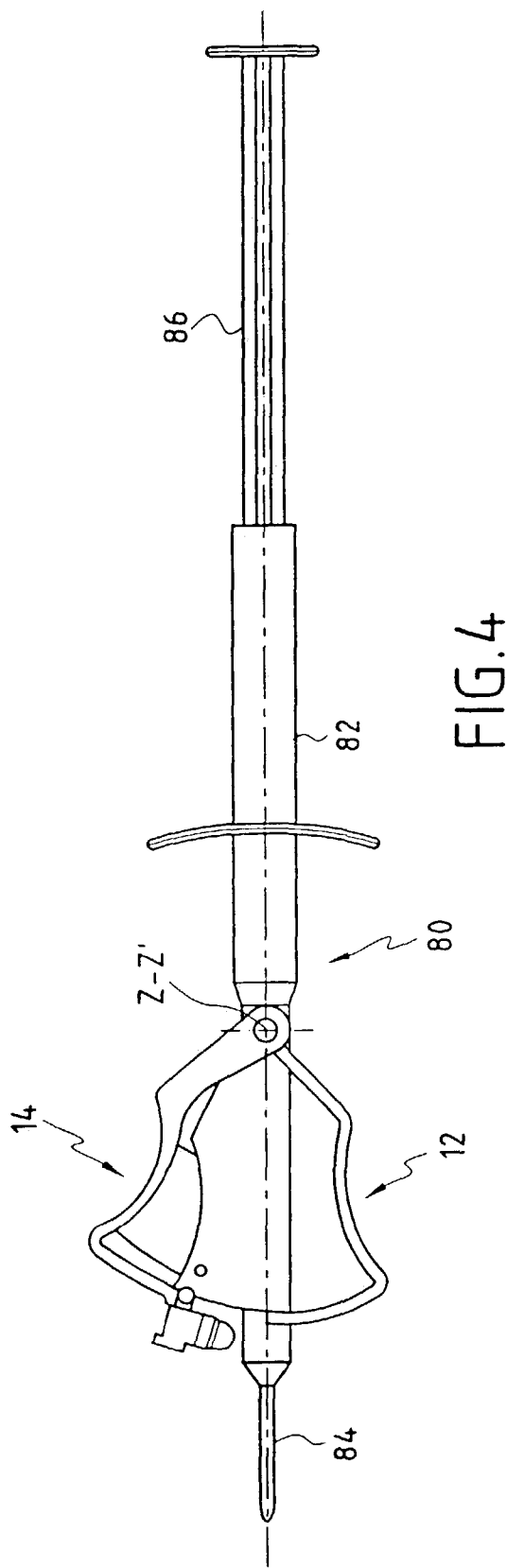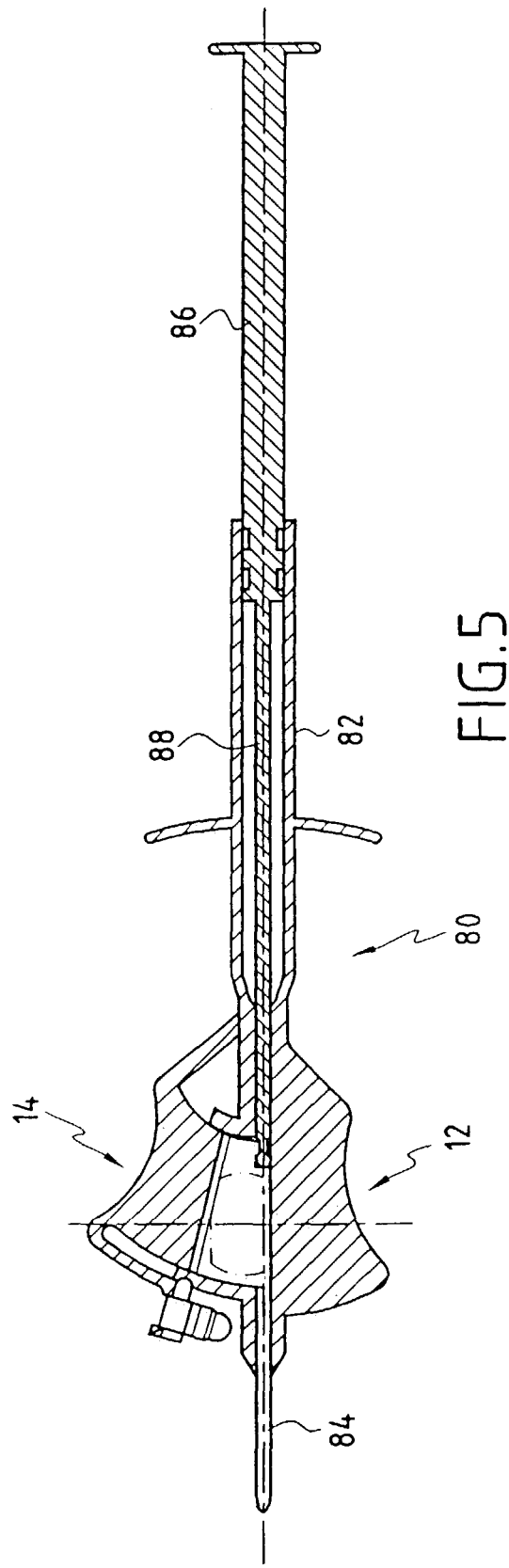

INJECTOR FOR A FLEXIBLE IMPLANT

CROSS-REFERENCE TO RELATED APPLICATIONS

This application is a Continuation of U.S. patent application Ser. No. 10/295,622, filed Nov. 15, 2002 now abandonded, which claims priority from Applications filed in France on May 19, 2000, No. 0006417 and with the PCT on May 17, 2001, No. PCT/FR01/01510.

The present invention relates to a folder module for folding a flexible implant and to a flexible implant Injector using the older module.

BACKGROUND OF THE INVENTION

Flexible implants are usually made of polyhydroxyethyl methacrylate (pHEMA) or of a silicone-based material presenting the essential feature that since the optical portion of such an implant is made out of such a flexible material, the implant and in particular its optical portion can be folded so as to reduce its transverse dimensions and thus enable the implant to be inserted into the eye through an incision made in the cornea, said incision being very small in size, typically about 3 millimeters (mm).

Such flexible implants are particularly advantageous in that novel techniques for removing the natural lens now require an incision to be made in the lens that is of small size only, about 3 mm when using the technique of phacoemulsifcation.

Nevertheless, folding the implant which is constituted by a substantially circular optical portion and by a haptic portion, presents certain difficulties, in particular because of the small dimensions of an intraocular implant where the diameter of the optical portion is typically no more than 6 mm, given the nature of the material constituting the implant.

In order to enable the implant to be folded or rolled up prior to being inserted in the eye, various types of flexible implant injector have already been proposed that incorporate a folder unit for the implant.

The term "folding" the implant should be understood as covering any mechanical operation enabling the shape of the implant to be modified elastically, and in particular the shape of its optical portion, so as to reduce the transverse size of the implant, i.e. in a direction that is orthogonal to the diameter of the optical portion containing the haptic elements of the implant. This can comprise merely folding about a diameter of the optical portion, or folding that is more complex about axes that are parallel to said diameter, or indeed rolling up about an axis parallel to said diameter.

It will be understood that once the implant has been folded, it suffices to place a cannula in the incision in the eye, said cannula extending the folder unit, and then to push the implant while it is in its folded shape through the cannula and into the inside of the eye.

Document WO 95/13022 describes a flexible implant injector comprising a folder unit which is constituted firstly by a folder chamber having a curved folder wall and two parallel walls, and secondly by a pusher acting on the proximal edge of the optical portion of the implant in a direction orthogonal to the folder wall, so that progressive displacement of the pusher causes the implant to be folded or rolled up.

Nevertheless, it has been found that that type unit for folding or rolling up an implant is poorly adapted, particularly when the implant has certain types of haptic portion. It will be understood that the haptic portion which is usually constituted by two distinct elements needs to be folded or rolled up in the same direction as the optical portion. Unfortunately, the haptic portion is of dimensions that are small relative to those of the optical portion and as a result it has weaker mechanical strength properties which make folding the haptic portion very difficult.

In addition, it is awkward to put the implant into the folder chamber of a known folder module, and proper positioning of the haptic portions is random.

OBJECTS AND SUMMARY OF THE INVENTION

An object of the present invention is to provide a flexible implant folder module and a flexible implant injector using said folder module that make it possible to ensure that not only the optical portion but also the haptic portion of the intraocular implant can be folded or rolled up under improved conditions.

According to the invention, this object is achieved by a flexible implant folder module comprising:
  two jaws that are movable relative to each other, each jaw having a folder wall constituted by a portion of a cylindrical surface and a plane wall secured to the folder wall, the two plane walls lying in parallel planes;
  a pivot axis orthogonal to the plane walls to control relative pivoting movement of one jaw relative to the other;
  one of the jaws being capable of occupying relative to the other jaw a first position in which the plane walls are spaced apart from each other, thereby enabling the implant to be put into place on the bottom plane wall;
  a second position in which the plane walls face each other, whereby the folder walls and the plane walls define a confinement volume for the implant; and
  a third position in which the folder walls meet each other so as to define a substantially cylindrical volume forming a folder chamber enabling the implant to be finally folded.

Because of the relative pivoting movement of the two jaws about the pivot axis, the folder walls of the jaws do not make contact simultaneously with both elements of the haptic portion of the implant and with its optical portion. As explained in greater detail below, taking action on the various portions of the implant in this manner that is offset in time makes it possible to obtain appropriate folding of the implant as a whole, regardless of the shape of the elements constituting the haptic portion.

In addition, the implant is easy to put into place in the module when the two jaws are in their first relative position.

Preferably, the first of said jaws further comprises two side walls parallel to said pivot axis and secured to the edges of the plane wall of said jaw, such that when the two jaws are in their second relative position, the plane walls, the folder walls, and the side walls together define a "closed" storage space in which the implant can be held in a non-folded state.

By means of this disposition, the implant can be placed initially in the storage chamber, with the module then serving simultaneously as an element for confining the implant. The surgeon then need only remove the packaging from the module already fitted with its implant and bring the two jaws into their third relative position in order to be able to proceed with injecting the implant into the eye of a patient The invention also provides a flexible implant injector comprising:

a folder module;

an injector body including a housing for receiving said folder module, an injection cannula for extending said injection passage when said folder module is in place in said housing, and an axial guide duct for extending said guide passage when said folder module is in place in said housing; and a piston whose rod is slidably mounted in said axial guide duct, whereby the end of the rod of said piston can co-operate with one end of the pusher member of said folder module.

In a first embodiment of the injector, the folder module is removable from the injector body so that after the injector has been used it suffices to change the folder module in which the implant was initially stored. In a second embodiment, the folder module forms an integral portion of the injector and the entire injector needs to be changed on each use.

BRIEF DESCRIPTION OF THE DRAWINGS

Other characteristics and advantages of the invention appear more clearly on reading the following description of various embodiments of the invention given as non-limiting examples.

The description refers to the accompanying figures, in which:

FIG. 4 is a plan view of an implant injection of the invention;

FIG. 5 is a longitudinal section view of the FIG. 4 injector;

MORE DETAILED DESCRIPTION

Figure 1:
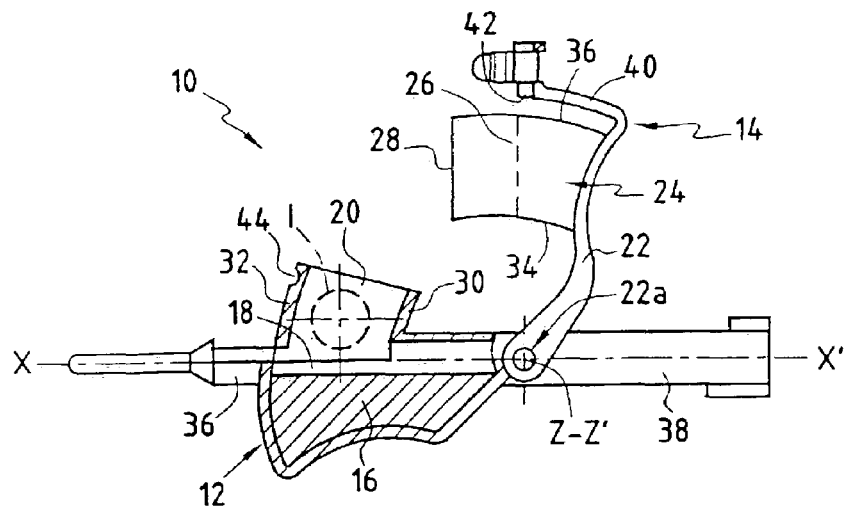
FIG. 1 is a fragmentary section view of a folder module in the open position.
Figure 2A:
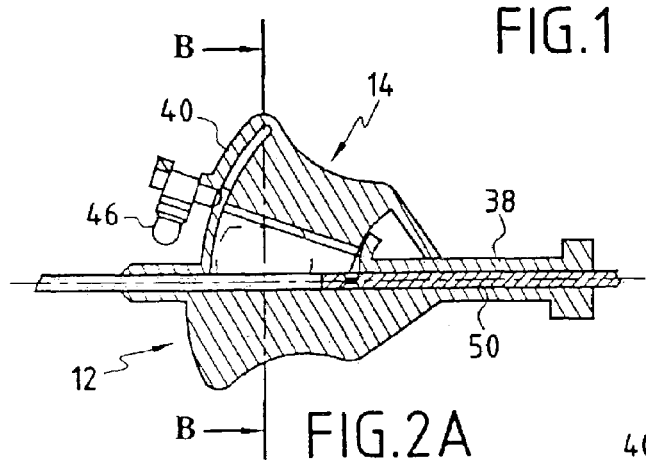
FIG. 2A is a longitudinal section view of the module in an intermediate open position.
Figure 3A:
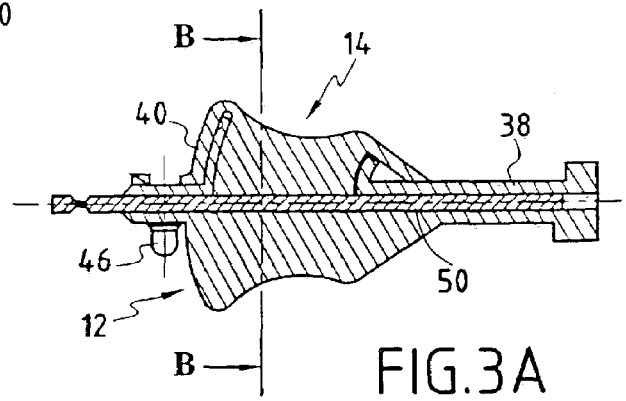
FIG. 3A is a longitudinal section view of the module in a final folding position.
Figure 2B:
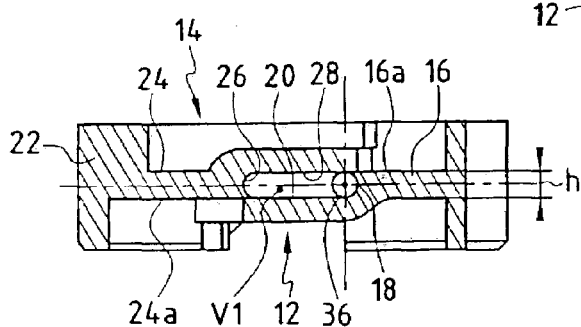
FIG. 2B is a section view on line B—B of FIG. 2A.
Figure 3B:
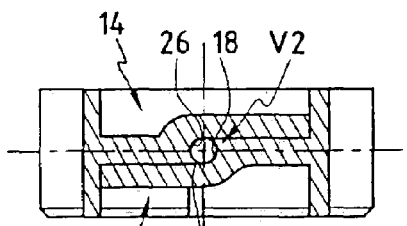
FIG. 3B is a section view on line B—B of FIG. 3A.

With reference initially to FIGS. 1 to 3, there follows a description of a preferred embodiment of the module for folding a flexible implant. The module 10 is essentially constituted by a first jaw 12 and by a second jaw 14 which are mutually pivotable about an axis. The first jaw 12 has a base 16 which defines a folder face 18 of semicylindrical shape on an axis X–X' together with an extension defining a plane face 20 which is connected tangentially to the folder face 18. The base 16 serves to connect the pivot axis Z–Z' which is orthogonal to the longitudinal axis X–X' to the folder face 18 and to the plane face 20. The second jaw 14 also comprises a base 22 which is in the form of an arm having one end 22a mounted to pivot about the axis Z–Z' and an extension 24 defining a folder face 26 that is substantially semicylindrical in shape, together with a plane face 28. These various portions can be seen more clearly in FIG. 2B. The first jaw 12 also has two ribs 30 and 32 disposed on either side of the plane face 20. These ribs 30 and 32 are in the form of circular arcs centered on the axis Z–Z'. In the same manner, the base 24 and the extension 26, 28 of the second jaw 14 have edges 34 and 36 in the form of circular arcs. The first jaw 12 also has a first injection passage 36 disposed on the axis X–X' and enabling the implant to be expelled after it has been folded, and a second guide passage 38 which enables a pusher member to slide so as to enable the folded implant to be introduced into the injection passage 36.

As shown better in FIG. 2B, the plane faces 20 and 28 of the two jaws are spaced apart by a distance h which is greater than the thickness of the implant to be folded and which corresponds to the outside diameter of the implant after it has been folded. The distance $\underline{h}$ corresponds to the inside diameter of the injection passage 36. $\underline{h}$ preferably lies in the range 1 mm to 3 mm. As also shown in FIG. 2B, the face 24a of the base 24 can slide over the plane face 20 of the other jaw, and the same applies to the face 16a of the base 16 and the plane face 28 of the other jaw.

In addition, the jaw pivot axis Z–Z' preferably intersects the axis X–X' of the jaw 12.

In FIG. 1, the second jaw 14 is shown in its position where it is spaced fully apart from the first jaw 12. In this position, it is easy to put an implant I into place so that it rests on the plane face 20 between the two side walls 30 and 32.

The jaw 14 can then be moved into a second position as shown in FIG. 2A in which the jaw 14 is partially engaged with the jaw 12. More precisely, the arm 22 of the jaw 14 has an extension 40 provided with a pip 42 which can co-operate with the notch 44 provided in the outside face of the side wall 32 of the jaw 12. The jaw 12 can thus be prevented from pivoting relative to the jaw 14 in a position such that the volume V1 defined by the folder faces 26 and 18 and by the plane faces 20 and 28, and by the side walls contain the implant I but without folding it. This position of the two jaws constitutes an implant-confinement position optionally allowing it to be stored for a reasonable length of time.

Furthermore, it should be observed that in this stage, and in the following stage (FIGS. 3A and 3B), the plane face of one jaw meets the semicylindrical face of the other jaw substantially tangentially. This avoids having any point of singularity when the two jaws are brought together.

The implant can be folded in the manner defined above by bringing the jaw 14 into a third position relative to the jaw 12 in which the two semicylindrical folder faces are adjacent so as to define an internal volume V2 of substantially cylindrical shape. On passing from the position shown in FIG. 2B to the position shown in FIG. 3B, it will be understood that the coming together of the folder faces of the two jaws causes the implant to be folded, with the implant being held between the plane faces 20 and 28. Depending on the nature and the dimensions of the implant, this folding can be folding substantially along a diameter of the optical portion of the implant, or folding that is more complex, or indeed it can comprise rolling the implant up about an axis parallel to the axis X–X'. The end of the extension 40 may have a snap-fastening system 46 co-operating with the outside face of the injection channel 36 to hold the jaw 14 in the position shown in FIG. 3A, i.e. in the injection position.

The folder module shown in FIGS. 1 to 3 is designed to be put into place in an injector body for actual injection of the implant. Under such circumstances, the guide channel 38 is fitted with a pusher 50 enabling the folded implant to be introduced into the guide channel 36 under drive from a piston fitted to the injector body.

Figure 7B:
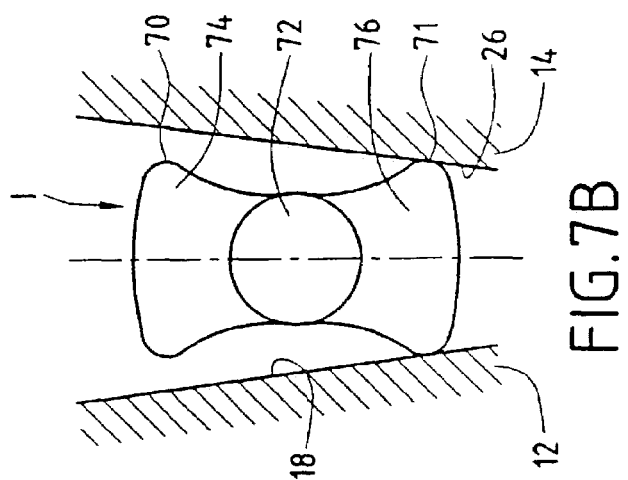
FIGS. 7A and 7B are diagrams showing how the implant is folded in a standard injector and in an injector in accordance with the invention.
Figure 7A:
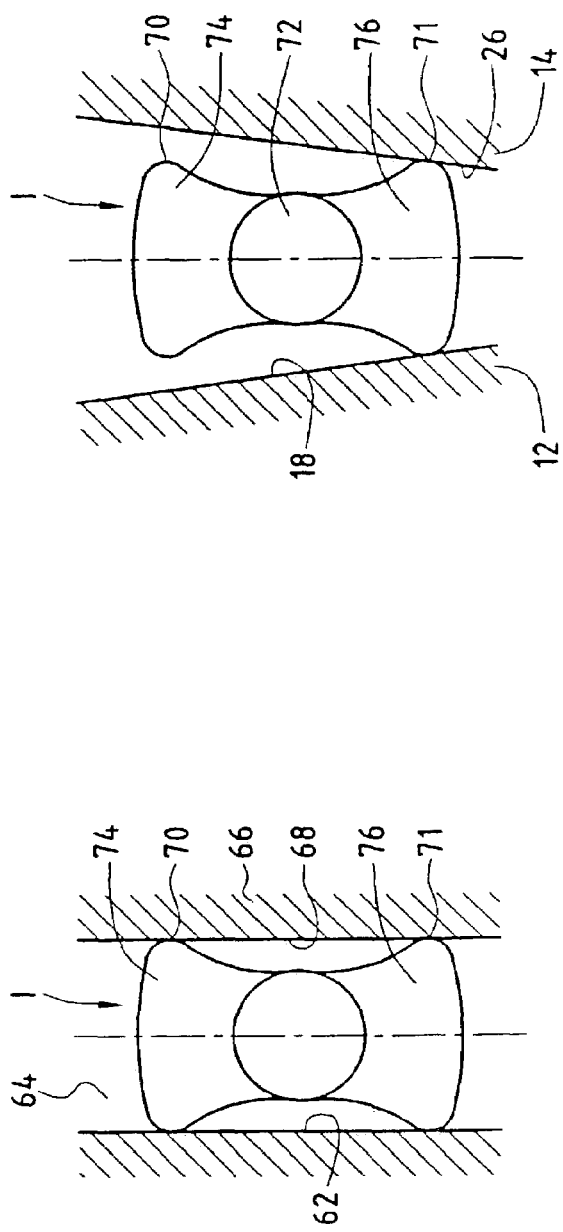

FIG. 7A shows an implant I being folded by a conventional type of folder module in which there is a folder chamber 60 defining a folder wall of semicylindrical shape 62 and two parallel walls, of which only the wall 64 is visible. Folding is obtained by movement in rectilinear translation along a direction orthogonal to the folder wall 62 of a pusher 66 whose active face 68 is likewise semicylindrical. During displacement of the pusher 66 in rectilinear translation, its folder face 68 acts simultaneously on the proximal edges 70 and 71 of the implant I, i.e. on its haptic portions 74 and 76. These proximal edges 70 and 71 are mechanically independent of each other. When the active face 68 of the pusher 66 comes into contact with one of the proximal edges, the folding or rolling up of the corresponding portion of the implant can take place randomly in one direction or the other. Since the two proximal edges 70 and 71 are mechanically independent, there is a risk that the direction in which folding or rolling up begins will be different for these two haptic portions 74 and 76. Having the two haptic portions folded in different directions runs the risk of spoiling the implant as implant folding continues with the pusher 36 coming closer to the folder face.

As shown in FIG. 7B which corresponds to the invention, the jaws 12 and 14 move relative to each other with pivoting motion. Consequently, as these two jaws move towards each other, the semicylindrical folder walls 18 and 26 come into contact initially with one of the haptic portions 76, then with the optical portion 72, and finally with the haptic portion 74, at least in the example shown. Because the folder walls make contact with the various portions of the implant in succession, a single direction of initial folding is obtained for one of the portions of the implant, and this folding direction is then transmitted to the other portions of the implant as the folder faces come to act thereon, thereby ensuring that the entire implant is folded in uniform manner.

Figure 6:
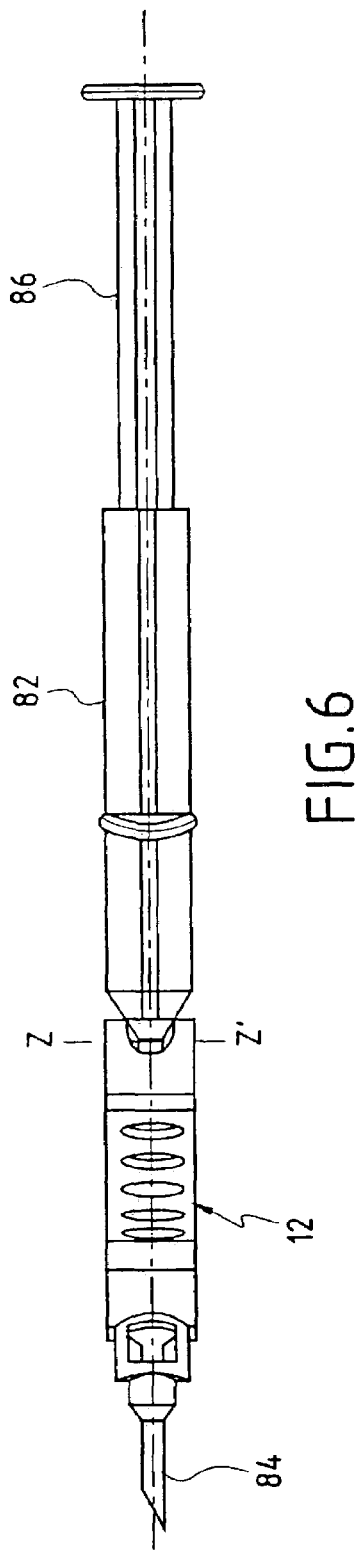
FIG. 6 is a side view of the FIG. 4 implant injector.

FIGS. 4 to 6 show an embodiment of a flexible implant injector 80 using a folder module of the type shown in FIGS. 1 to 3. The first jaw 12 is extended at one end by the body 82 of the injector. The opposite end of the jaw 12 is extended by a cannula 84 which in turn extends the injection passage 36 of the jaw. Under such circumstances, the pusher member is omitted and replaced by a piston 86 whose terminal portion 88 is of appropriate diameter and length to push a folded implant into the cannula 84.

What is claimed is:

1. A folder module for folding a flexible intraocular implant for injection into the eye of a patient, the module comprising:
   two jaws that are movable relative to each other, each jaw having a folder wall constituted by a portion of a cylindrical surface and a plane wall secured to the folder wall, the two plane walls lying in parallel planes, one of said plane walls forming a bottom plane wall;
   a pivot axis orthogonal to the plane walls to control relative pivoting movement of one jaw relative to the other;
   one of the jaws being capable of occupying relative to the other jaw a first position in which the plane walls are spaced apart from each other, thereby enabling the implant to be put into place on the bottom plane wall; a second position in which the plane walls face each other, whereby the folder walls and the plane walls define a confinement volume for the implant; and a third position in which the folder walls meet each other so as to define a substantially cylindrical volume forming a folder chamber enabling the implant to be finally folded.

2. A folder module according to claim 1, wherein the first of said jaws further comprises two side walls parallel to said pivot axis and secured to the edges of the plane wall of said jaw, such that when the two jaws are in their second relative position, the plane walls, the folder walls, and the side walls together define a storage space in which the implant can be held in a non-folded state.

3. A folder module according to claim 2, wherein the distance between the two plane walls is greater than the thickness of the implant.

4. A folder module according to claim 3, wherein the distance between the plane walls lies in the range 1 mm to 3 mm.

5. A folder module according to claim 2, wherein said jaws further comprise means for holding them in their second relative position, whereby the implant can be held in a storage volume.

6. A folder module according to claim 2, wherein said jaws further comprise holding means for holding them in their third relative position, whereby the implant can be held in the folded state in the folder chamber so as to enable the implant to be injected into the eye of a patient.

7. A folder module according to claim 2, wherein said first jaw further comprises an injection passage at one of the ends of said folder chamber on an axis that substantially coincides with the axis of the cylindrical volume defined by the folder walls when said two jaws are in their third relative position.

8. A folder module according to claim 7, wherein said first jaw further comprises a guide passage opening out to the second end of the folder chamber and having the same axis as the folder chamber, and a pusher member slidably mounted in the guide passage for pushing the implant in the folded state into said injection passage.

9. A flexible implant injector comprising: a folder module comprising:
   two jaws that are movable relative to each other, each jaw having a folder wall constituted by a portion of a cylindrical surface and a plane wall secured to the folder wall, the two plane walls lying in parallel planes, one of said plane walls forming a bottom plane wall;
   a pivot axis orthogonal to the plane walls to control relative pivoting movement of one jaw relative to the other; one of the jaws being capable of occupying relative to the other jaw a first position in which the plane walls are spaced apart from each other, thereby enabling the implant to be put into place on the bottom plane wall; a second position in which the plane walls face each other, whereby the folder walls and the plane walls define a confinement volume for the implant; and a third position in which the folder walls meet each other so as to define a substantially cylindrical volume forming a folder chamber enabling the implant to be finally folded;
   said first jaw further comprising: an injection passage at one of the ends of said folder chamber on an axis that substantially coincides with the axis of the cylindrical volume defined by the folder walls when said two jaws are in their third relative position; and a guide passage opening out to the second end of the folder chamber and having the same axis as the folder chamber, and a pusher member slidably mounted in the guide passage for pushing the implant in the folded state into said injection passage;
   an injector body including a housing for receiving said folder module, an injection cannula for extending said injection passage when said folder module is in place in said housing, and an axial guide duct for extending said guide passage when said folder module is in place in said housing; and a piston whose rod is slidably mounted in said axial guide duct, whereby the end of the rod of said piston can co-operate with one end of the pusher member of said folder module.

10. A flexible implant injector comprising: a folder module comprising:
two jaws that are movable relative to each other, each jaw having a folder wall constituted by a portion of a cylindrical surface and a plane wall secured to the folder wall, the two plane walls lying in parallel planes, one of said plane walls forming a bottom plane wall;
a pivot axis orthogonal to the plane walls to control relative pivoting movement of one jaw relative to the other; one of the jaws being capable of occupying relative to the other jaw a first position in which the plane walls are spaced apart from each other, thereby enabling the implant to be put into place on the bottom plane wall; a second position in which the plane walls face each other, whereby the folder walls and the plane walls define a confinement volume for the implant; and a third position in which the folder walls meet each other so as to define a substantially cylindrical volume forming a folder chamber enabling the implant to be finally folded; a cannula extending a first end of said confinement chamber to guide the implant in its folded state; a guide passage extending a second end of said guide chamber; and a piston slidably mounted in said guide passage to push the implant in the folded state from said folder chamber into said cannula.

* * * * *